(12) United States Patent
Ikegami (10) Patent No.: US 9,589,174 B2
(45) Date of Patent: Mar. 7, 2017

(54) IMAGING MASS SPECTROMETER AND MASS SPECTROMETRY DATA PROCESSING METHOD

(75) Inventor: Masahiro Ikegami, Takaishi (JP)

(73) Assignee: Shimadzu Corporation, Kyoto (JP)

( * ) Notice: Subject to any disclaimer, the term of this patent is extended or adjusted under 35 U.S.C. 154(b) by 1066 days.

(21) Appl. No.: 13/565,565

(22) Filed: Aug. 2, 2012

(65) Prior Publication Data

US 2013/0080072 A1 Mar. 28, 2013

(30) Foreign Application Priority Data

Sep. 26, 2011 (JP) ................. 2011-208770

(51) Int. Cl.
*H01J 49/26* (2006.01)
*G06K 9/00* (2006.01)
*G06F 19/24* (2011.01)
*H01J 49/00* (2006.01)

(52) U.S. Cl.
CPC ...... *G06K 9/00134* (2013.01); *H01J 49/0004* (2013.01); *G06F 19/24* (2013.01)

(58) Field of Classification Search
CPC ... G06K 9/00134; H01J 49/0004; G06F 19/24
See application file for complete search history.

(56) References Cited

U.S. PATENT DOCUMENTS

2007/0114388 A1* 5/2007 Ogawa ............... H01J 49/0004
250/288

OTHER PUBLICATIONS

Imaging of Colorectal Adenocarcinoma using FT-IR Microspectroscopy and Cluster Analysis. Lasch et al. Biochimica et Biophysica Acta 1688 (2004).*

* cited by examiner

Primary Examiner — Manuel L Barbee
Assistant Examiner — Timothy McMahon
(74) Attorney, Agent, or Firm — Morgan, Lewis & Bockius LLP (57) ABSTRACT

Specific-site extraction unit 24 extracts specific sites from microscopy images that are obtained by staining or fluorescence labeling of specific sites in a specimen 4. Based on the similarity between MS imaging data and the spatial distribution of the specific sites, cluster analysis unit 25 and division count determination processing unit 26 evaluate the similarity with the spatial distribution of all pixels that belong to one cluster when each of the pixels are categorized into a plurality of clusters. Since the specific sites are sites that include the same characteristic substance, clustering is judged to be appropriate if the similarity in spatial distribution is high. Hence, based on the correlation between spatial distributions, an appropriate division count for the cluster analysis is determined, and the result of the cluster analysis using the division count is output on a display unit 31.

10 Claims, 7 Drawing Sheets

STAINED IMAGE

FIG.5B

STAINED IMAGE AFTER
PIXEL ADJUSTMENT

FIG.6A
STAINED IMAGE AFTER PIXEL ADJUSTMENT

SPECIFIC SITE

FIG.6B
CLUSTER DISTRIBUTION IMAGE BASED ON MS IMAGING DATA

NUMBER OF DIVISIONS: 2 → $A_n = 4$

CLUSTER CORRESPONDING TO SPECIFIC SITES

FIG.6C
NUMBER OF DIVISIONS: 3 → $A_n = 17$

FIG.6D
NUMBER OF DIVISIONS: 4 → $A_n = 7$

FIG.7

IMAGING MASS SPECTROMETER AND MASS SPECTROMETRY DATA PROCESSING METHOD

FIELD OF THE INVENTION

The present invention relates to an imaging mass spectrometer capable of obtaining mass spectrometry imaging images that show the strength distribution of a specific mass/charge ratio (m/Z) signal within a two-dimensional area of a specimen and also relates to a mass spectrometry data processing method for processing mass spectrometry data obtained with said mass spectrometer.

BACKGROUND OF THE INVENTION

Mass spectrometry imaging ("rms imaging") is a method for investigating the distribution of substances having a specific mass/charge ratio by performing mass spectrometry in a plurality of micro-regions within a two-dimensional area of a specimen such as a piece of biological tissue. Much hope is pinned on the use of mass spectrometry imaging in fields such as drug discovery, search for biomarkers and the determination of causes for different illnesses and diseases. Mass spectrometers that are used for performing MS imaging are generally referred to as imaging mass spectrometers since ordinarily a microscopy imaging is performed over an optional range of a specimen to determine the region where analysis would be performed based on the microscopy images and imaging mass spectrometry is then performed over the region that is so determined. For example, Non-Patent Literature 1 discloses the configuration of usual imaging mass spectrometers and examples of analysis performed using them.

With imaging mass spectrometers, mass spectrometry data (MS spectrum data and MS" spectrum data) is obtained from each of numerous measurement points (micro-regions) located within a two-dimensional area of a specimen. The amount of mass spectrometry data that is obtained from any one measurement point increases as mass resolution is increased. Furthermore, since the distance between the measurement points on the specimen affects spatial resolution, increasing the spatial resolution to obtain finer MS imaging images increases the number of measurement points, and this, in turn, increases the amount of mass spectrometry data that is obtained from the two-dimensional area that is being measured. Because of this relationship, the amount of MS imaging data that is obtained usually becomes voluminous. This means that, for a person performing the analysis, finding meaningful information from the voluminous amount of MS imaging data requires much time and labor. In general, because the strength information of specific mass/charge ratio at any one measurement point is represented in a MS imaging image as color information or shading information for individual pixels, the term "pixel" is used hereinafter to refer to a measurement point.

To solve the afore-described problem, attempts have been made to perform computer-aided statistical analysis on MS imaging data to extract meaningful information. Specifically, support vector machines (SVM) and cluster analysis, which is a method of multivariate analysis, are performed on MS imaging data obtained from biological specimen including cancerous tissues and normal tissues to see whether cancerous tissues and normal tissues can be identified in a specimen (see Non-Patent Literature 2 and 3).

With cluster analysis, the shape of the mass spectrum at each pixel is used as a basis for determining and categorizing, that is, clustering, whether a pixel represents a cancerous tissue, a normal site or some other site. When performing cluster analysis, a more detailed categorization based on the condition of the tissue/site is possible by using a greater division count for the tissue/site, that is, by increasing the total number of clusters and setting it to a large value. However, a downside to doing this is that the categorization can become more susceptible to the effects of for example, foreign components. Slight variations in foreign components may cause the same tissue to be categorized into different clusters, and the categorization tends to become inaccurate. An algorithm that is known with cluster analysis automatically calculates the total cluster count that is estimated to be the most appropriate based on, for example the k-means method, and uses the total cluster count for categorizing each of the pixels.

However, when normal tissue and pathological tissue that are present in a biological specimen have to be distinguished from each other, the difference in mass spectrum of the two is often not very clear because of the prevalence of substances that are commonly present in both. This prevents the reliability of the afore-described total cluster count that is automatically calculated from being very high. Because of this, the categorization result is usually no better than to serve just as a rough guideline, and ultimately, a person has to judge the correctness of the categorization results. If the categorization is inappropriate, the person has to manually specify the total cluster count and repeat the analysis. Furthermore, the judgment that has to be exercised owes much to experience and skill of the person performing the analysis, creating a factor that causes the final result to vary depending on the person performing the analysis.

On the other hand, if SVM is used, reference data (referred to as "training data") that is representative of normal sites and cancerous tissues are stored in memory in advance, and individual pixels are categorized based on the reference data. This requires that the person performing the analysis select training data for the specific sites of interest representing cancerous tissues and the like. However, selecting the correct training data is not easy. Also, just as with cluster analysis, the correctness of the categorization result ultimately has to be judged by a person performing the analysis. Again, the accuracy of the analysis result ultimately depends largely on the skill and experience of the person performing the analysis.

Non-Patent Literature 1: Harada and 8 others, "Analysis of Biological Tissues Using Imaging Mass Spectrometer," Shimadzu Hyouron, Vol. 64, 3rd and 4th issues, published Apr. 24, 2008, pp. 139-145

Non-Patent Literature 2: Gregor McCombie and 3 others, "Spatial and Spectral Correlations in MALDI Mass Spectrometry Images by Clustering and Multivariate Analysis," Analytical Chemistry, 2005, Vol. 77, pp. 6118-6124

Non-Patent Literature 3, Kristina Schwamborn and 5 others, "Identifying Prostate Carcinoma by MALDI-Imaging," International Journal of Molecular Medicine, 2007, Vol. 20, pp. 155-159

SUMMARY OF THE INVENTION

The present invention was made in light of the afore-described problems, and it is the primary object of the present invention to allow division count used for cluster analysis to be correctly set so that, when cluster analysis is performed to identify specific sites or investigate their distribution in a specimen using an imaging mass spectrometer, different characteristic sites that are present within the specimen are correctly categorized. Another object of the present invention is to allow appropriate training data to be specified without depending on the judgment of the person performing the analysis so that, when SVM is performed to identify specific sites or investigate its distribution in a specimen using an imaging mass spectrometer, different characteristic sites that are present within the specimen are correctly categorized.

With the observation of biological specimens, visualization markers are often used to label specific tissues or specific molecules for their observation\detection. For example, a specific site within a specimen may be stained using a staining reagent that easily binds with a specific substance so that the specific site expresses itself in a different color from other sites. Alternatively, antibodies that are labeled with a fluorescent dye or a fluorescent pigment can be introduced into the specimen so that a specific site within the specimen is fluorescently labeled and observed with fluorescent microscopy. Even if sites that have been labeled with a visualization marker in this way are scattered through a specimen, these are the same specific sites and can be considered to be sites that should be clustered in the same cluster in a cluster analysis. This has caused the inventors of the present application to realize that the information that is available in observed images of a specimen that is labeled with visualization markers can be used to determine whether the division or the division count that is used for cluster analysis or SVM is appropriate or not.

To explain, a first invention that was made to solve the afore-described problems is a mass spectrometry data processing method for processing mass spectrometry data that is obtained from each of a plurality of micro-regions that are set within a predetermined two-dimensional area on a specimen, the method comprising:

a) a specific-site extraction step for extracting specific sites from microscopy images, which are obtained by labeling specific sites in the two-dimensional area or a portion thereof with a visualization marker;

b) an analysis processing step for categorizing each of the micro-regions into a plurality of clusters based on similarity/dissimilarity of mass spectrometry data for each of the micro-regions so that micro-regions of a high similarity belong to the same cluster; and c) a division count determination step for determining the total number of clusters used in the analysis processing step based on the results of a comparison between the spatial distribution of specific sites that are extracted by the specific-site extraction step and the spatial distribution of all micro-regions that belong to one of the plurality of clusters into which each of the micro-regions are classified in the analysis processing step.

The second invention that was made to solve the afore-described problems is an imaging mass spectrometer for practicing the mass spectrometry data processing method according to the first invention and for obtaining mass spectrometry data from each of a plurality of micro-regions that are set within a predetermined two-dimensional area on a specimen, the spectrometer comprising:

a) an image-capturing means for acquiring microscopy images of a specimen wherein specific sites that are present within said two-dimensional area or a portion thereof have been marked with a visualization marker;

b) a specific-site extraction means for extracting said specific sites from microscopy images that have been acquired by the image-capturing means;

c) an analysis processing means for categorizing each of the micro-regions into a plurality of clusters based on similarity/dissimilarity of mass spectrometry data for each of the micro-regions so that micro-regions of a high similarity belong to the same cluster; and d) a division count determination means for determining the total number of clusters used by the analysis processing means based on the results of a comparison between the spatial distribution of specific sites that are extracted by the specific-site extraction means and the spatial distribution of all micro-regions that belong to one of the plurality of clusters into which each of the micro-regions are classified by the analysis processing means.

In the first and the second inventions (and also in the third and fourth inventions further described below), the "specimen" typically is derived from a biological organism such as a piece of biological tissue, and if that is the case, the term "specific site" refers to a specific biological tissue or a pathological tissue such as cancer.

Labeling with a visualization marker refers to the process of staining a specific tissue or specific substance with a staining reagent and the like, or the process of causing a fluorescent substance to bind to or to be introduced into a specific tissue or specific substance. In the case of the latter, a fluorescence microscopy is performed, instead of optical microscopy to obtain fluorescence microscopy images.

Because, as afore-described, labeling using visualization markers such as staining is performed on a specific tissue or specific substance, many of the same substances will be present in specific sites that have been visualized by labeling. This means that mass spectrometry data, more specifically, for example, mass spectrum data (or $MS^n$ spectrum data) or peak lists derived therefrom by waveform processing, which are obtained from micro-regions that correspond to the aforesaid specific sites in the specimen, will have a high degree of similarity. In other words, after clustering is performed in an analysis processing step so that micro-regions that exhibit mass spectrometry data of a high similarity belong to the same cluster, if it turns out that the spatial distribution of said specific sites closely matches the spatial distribution of all micro-regions that belong to any one cluster, this can be understood as indicating a high likelihood that the clustering has correctly divided the respective sites on the specimen. Therefore, with the division count determination step, the spatial distribution of all micro-regions that belong to one cluster among a plurality of clusters that are generated by clustering is compared against the spatial distribution of the aforesaid specific sites, and if the spatial distributions are close, a judgment is made that the total cluster count used for the clustering is an appropriate total cluster count.

As a specific mode of practicing the invention, the division count determination step evaluates the correlation between the spatial resolution of all micro-regions that belong to one of a plurality of clusters and the spatial distribution of specific sites that are extracted by the specific-site extraction step and determines as the appropriate total cluster count either the sole total cluster count with the highest correlation or a predetermined number of total cluster counts that are selected after ranking them in the order of high to low correlation. As for evaluating the correlation, this can be done by determining an index value that indicates the level of correlation according to a predetermined rule and selecting a total cluster count that maximizes the index value, or a prescribed number of total cluster counts can be selected according to a ranking of the index value from high to row.

Furthermore, because cluster analysis logarithms generally include a function to calculate the optimum (highest certainty) division count, this function can be used to narrow down the range for searching the division count. To explain, as one mode of the present invention, the analysis processing step may determine the optimum total cluster count when categorizing each of the micro-regions into a plurality of clusters, and the division count determination step may use the optimum total cluster count as a guideline for a predetermined range of total cluster counts and the spatial distribution of specific sites to determine the appropriate total number of clusters.

Furthermore, the specific sites need not be limited to just one type. The spatial distribution of each of a plurality of types of specific sites and the spatial distribution of all micro-regions that belong to each cluster among a plurality of clusters can be compared, and a total cluster count with the highest possibility can be selected from the results of the comparison. Still furthermore, the site that is labeled with a visualization marker need not necessarily be a tissue or site whose distribution has to be confirmed based on imaging mass spectrometry. Instead, any site of interest can be selected by the person performing the analysis.

Comparing the spatial distribution of a specific site and the spatial distribution of all micro-regions that belong to one cluster requires that the correspondence between the positions of each microscopic region for which mass spectrometry data has been obtained and the position on the microscopy images be clearly known. For this purpose, the method, for example, that is disclosed in International Publication Pamphlet No. 2008/068847 can be used to register the positions so that no positional shifting occurs between the time when microscopy images are captured and when imaging mass spectrometry is performed, or to correct any positional shifting that occurs.

The afore-described first and second inventions are used for the statistical processing of mass spectrometry data using cluster analysis. However, when processing mass spectrometry data using a statistical learning method such as a support vector machine, information on specific sites that have been extracted from microscopy images can be used for selecting reference data to be used for learning.

To explain, the third invention that was made to solve the afore-described problems is a mass spectrometry data processing method for processing mass spectrometry data obtained from each of a plurality of micro-regions that are set within a predetermined two-dimensional area on a specimen, said method comprising:

a) a specific-site extraction step for extracting specific sites from microscopy images, which are obtained by labeling specific sites in the two-dimensional area or a portion thereof with a visualization marker;

b) an analysis processing step for categorizing each of the micro-regions into a plurality of groups by using as reference data the mass spectrometry data that was obtained from micro-regions on the specimen that are included in a range of specific sites that were extracted by the specific-site extraction step and by using a statistical learning method that is based on the reference data.

The fourth invention that was made to solve the afore-described problem is an imaging mass spectrometer for practicing the mass spectrometry data processing method according to the third invention and which obtains mass spectrometry data from each of a plurality of micro-regions that are set within a predetermined two-dimensional area of a specimen, the imaging mass spectrometer comprising:

a) an image-capturing means for acquiring microscopy images of a specimen wherein specific sites that are present within the two-dimensional area or a portion thereof have been marked with a visualization marker;

b) a specific-site extraction means for extracting said specific sites from microscopy images that have been acquired by the image-capturing means; and c) an analysis processing means for categorizing each of the micro-regions into a plurality of groups by using as reference data the mass spectrometry data that was obtained from micro-regions on the specimen that are included in a range of specific sites that were extracted by the specific-site extraction means and by using a statistical learning method that is based on the reference data.

As used here, "statistical learning method" typically refers to a support vector machine.

Furthermore, with the third and fourth inventions, the spatial distribution of specific sites can be used to determine whether or not the grouping of micro-regions based on a statistical learning method is appropriate or not. To explain, just as with the first and second inventions, the spatial distribution of specific sites and the spatial distribution of all micro-regions belonging to one group among a plurality of groups are compared, and a determination is made based on the result of the comparison as to whether or not the grouping is appropriate. The result of the determination can be output, or if a determination is made that the grouping is not appropriate, mass spectrometry data that is obtained from different micro-regions of the specimen that are included in a range of specific sites can be used as a reference data to repeat the grouping.

With the mass spectrometry data processing method according to the first invention and the imaging mass spectrometer according to the second invention, even when measuring a specimen with a complicated structure of numerous tissues or sites, or even when it is difficult to find a substance that characterizes a tissue or a site because of the uniform presence of a common substance throughout the measured region, it is possible to obtain a total cluster count that can appropriately divide each tissue or site to perform a cluster analysis. Furthermore, even when it is not possible to narrow down the total cluster count to a single value, it is possible to inform the person performing the analysis of a plurality of cluster analysis results that presents a high likelihood of the total cluster count being appropriate, thus allowing the person performing the analysis to select an optimum clustering in a more efficient manner as compared to the past and reducing the burden being placed on the person. This allows, for example, the distribution of pathological tissue in a specimen to be more accurately understood.

Furthermore, with the mass spectrometry data processing method according to the third invention and the imaging mass spectrometer according to the fourth invention, it is possible to more accurately understand the distribution of substances that correspond to specific sites on the specimen.

BRIEF DESCRIPTION OF THE DRAWINGS

FIGS. 5A and 5B show a conceptual view of the pixel adjustment process used in the present embodiment of an imaging mass spectrometer.

FIGS. 6A-6D show each a conceptual view of the division count determination processing used in the present embodiment of an imaging mass spectrometer. FIG. 6 (A) shows a stained image after pixel adjustment.

DETAILED DESCRIPTION OF THE INVENTION

Figure 1:
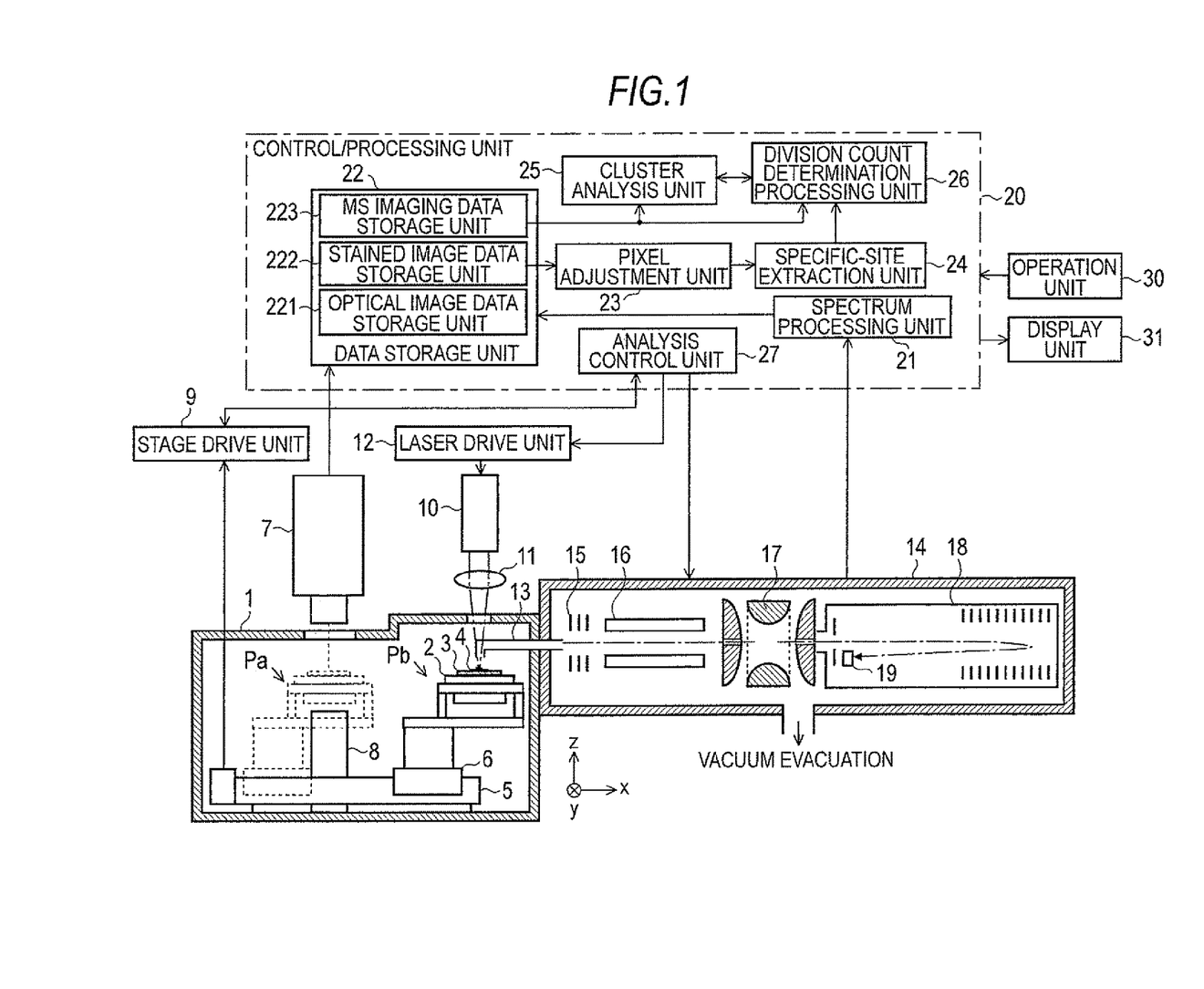
FIG. 1 shows a schematic view of the major components of one embodiment of an imaging mass spectrometer according to the present invention.

An embodiment of an imaging mass spectrometer according to the present invention is described next with reference to the attached drawings. FIG. 1 shows the major components of the present embodiment of the imaging mass spectrometer.

The imaging mass spectrometer comprises: a hermetically sealed chamber 1 whose interior is kept substantially at atmospheric pressure; and a vacuum chamber 14 whose interior is kept at a high degree of vacuum by a vacuum pump that is not illustrated such as a turbo molecular pump. Disposed within the hermetically sealed chamber 1 is a specimen stage 2 which holds a specimen plate 3 with a specimen 4 placed thereon, the specimen stage 2 reciprocatingly sliding over a large distance in the X-direction along guide 5 by means of a drive mechanism 6 that includes a motor and the like. In FIG. 1, the position where specimen stage 2 is drawn with solid lines is analysis position Pb while the position drawn with dotted lines is observation position Pa.

In addition to moving in the X-direction along guide 5 as dictated by the drive mechanism 6, which is driven by stage drive unit 9, the specimen stage 2 can also move over a predetermined range in the Y-direction, which is orthogonal to the X-direction in the horizontal direction, and also over a predetermined range in the Z-direction, which is in the height direction.

An image-capturing unit 7 comprising CCD camera, lenses and the like is disposed above the observation position Pa outside the hermetically sealed chamber 1. A transmitted-illumination unit 8 is disposed within the hermetically sealed chamber 1 at a position opposite to the image-capturing unit 7. When the specimen stage 2 is situated at observation position Pa, light that is emitted from the transmitted-illumination unit 8 passes through an opening that is formed in the specimen stage 2 and becomes incident to the bottom surface of the specimen 4. The specimen image that is created by the transmitted light can be observed by means of the image-capturing unit 7. The magnification factor of the microscopy that is performed with the image-capturing unit 7 is variable over a predetermined range. The higher the magnification factor, the more finely the surface of the specimen 4 can be observed but at the expense of the observable range. That is, the observation field of view becomes smaller as the magnification factor is increased.

The image data that is captured with the image-capturing unit 7 is sent to the control/processing unit 20 further described below. In addition to such transmitted observation, it is also possible to provide additional illumination for reflection observation or fluorescence observation.

A laser beam irradiation unit 10, driven by a laser drive unit 12, and a laser focusing optical system 11 are disposed above the analysis position Pb outside the hermetically sealed chamber 1 for shining a laser beam that has been focused to a microscopic diameter onto the surface of the specimen 4. Also disposed within the interior of the hermetically sealed chamber 1 to face specimen 4 is an ion collection opening of ion transport tube 13 for transporting to a vacuum chamber 14 ions that are generated from specimen 4 by the irradiation with the laser beam.

The laser beam used for ionization that is emitted from the laser beam irradiation unit 10 under the control of analysis control unit 27, which is included within the control/processing unit 20, is focused by the laser focusing optical system 11 and is irradiated onto the specimen 4. The diameter of the laser beam that is irradiated onto specimen 4 is microscopic, for example, 1 μm to several dozen μm. When the specimen stage 2 is moved within the X-Y plane as afore-described by the drive mechanism 6, the position on the specimen 4 that is irradiated by the laser beam changes, that is, the position of the micro-regions on specimen 4 that are subjected to mass spectrometry moves. This means that the position on specimen 4 where mass spectrometry is performed is two-dimensionally scanned, and mass spectrometry is performed on each microscopic region (measurement point) that is partitioned in a grid-like pattern on a two-dimensional area having any shape of choice.

Disposed within the vacuum chamber 14 are: ion transport optical systems 15 and 16 for converging the ions and sending them to a later stage; an ion trap 17 for temporarily holding the ions; a Reflectron-type time-of-flight mass spectrometer 18 for separating the ions according to the mass/charge ratio (m/Z); and a detector 19 for detecting the ions that have been separated by the time-of-flight mass spectrometer 18. Here, the ion transport optical systems 15 and 16 comprise a combination of an electrostatic electromagnetic lens and a multi-pole radio-frequency ion guide. However, this combination is not a limitation, and other configurations may be used. The ion trap 17 has a 3-dimensional quadrupole configuration, and its function is not just to hold ions but to also select ions having a specific mass/charge ratio from among various ions that are introduced into it and to generate product ions by causing cleavage by collision induced dissociation (CID). In other words, in addition to ordinary mass spectrometry (not accompanied by a cleavage), this imaging mass spectrometer can also perform MS/MS analysis and $MS^n$ analysis.

The image data that is sent from the image-capturing unit 7 to the control/processing unit 20 is stored as necessary in optical image data storage unit 221 or stained image data storage unit 222 of data storage unit 22. In addition to spectrum-processing unit 21 for processing the detection signal that is sent from detector 19, the control/processing unit 20 comprises such functional blocks as: pixel adjustment unit 23; specific-site extraction unit 24; cluster analysis unit 25; and division count determination processing unit 26. The data storage unit 22 includes a MS imaging data storage unit 223. Furthermore, connected to the control/processing unit 20 are operation unit 30 which is operated by the person performing the analysis and a display unit 31 for displaying the results of the analysis and the like.

At least a portion of the functions of the control/processing unit 20 can be executed by dedicated software that is installed and runs on a personal computer. In that case, the different units that are included in the control/processing unit 20 are functional blocks that are executed by software.

With the present embodiment of the imaging mass spectrometer, in analyzing and processing the MS imaging data for a predetermined area of a specimen, stained microscopy images are used wherein the specific sites are labeled with visualization markers to visually differentiate them from other sites in the same region on the same specimen 4. In this example, a staining reagent was used as a visualization marker for labeling, but the labeling method is not limited to this. For example, a fluorescent dye that uses a fluorescent dye reagent, an antibody fluorescent dye that introduces an antibody labeled with a fluorescent pigment into a specific substance, and a method that uses genetic modification to introduce a gene that guides fluorescent protein such as green fluorescent protein (GFp) into a target substance can be used to stain a specific site or specific tissue in a specimen with a fluorescent dye. Fluorescence microscopy images of the specimen that are obtained by observation with fluorescence microscopy can then be used.

First, the procedure by which MS imaging data and stained microscopy image data are obtained for specimen 4 is explained. To perform matrix coating or staining for mass spectrometry, the specimen 4 has to be removed and placed back on the specimen stage 2. So that the same location can be observed and measured without any positional shifting, the method that is disclosed in International Publication No. 2008/068847 is used. To explain, two markings separated by a predetermined distance are provided on specimen plate 3 (or on a specimen holder that is not illustrated but holds specimen plate 3). By recognizing the position of these markers, the amount and direction (angle) of any positional shifting of specimen 4 on the specimen stage 2 are recognized. Positional shifting is corrected based on this.

To capture with the image-capturing unit 7 at observation position Pa optical microscopy images of the specimen 4 prior to performing a pre-process, image capturing is performed so that markings on the specimen plate 3 are captured. The control/processing unit 20 performs image recognition on the optical microscopy images with the markings captured. The positional coordinates of the markings on the image are calculated, and the coordinates are determined with respect to a specific reference position of the mass spectrometer. Also, the inclination angle in the horizontal plane of the specimen plate 3 is calculated based on the position coordinates of the two markings. Information regarding position coordinates and rotation angle of the markings are associated with the optical microscopy image data and are stored in optical image data storage unit 221.

After the images are captured, the person performing the analysis removes the specimen plate 3 from the specimen stage 2 and attaches a matrix to the top surface of the specimen 4. Masking and the like are performed on the marking portions of specimen plate 3 so that the matrix does not adhere to the marking portions. After the matrix is added, the specimen plate 3 is returned to the specimen stage 2, and optical microscopy images are obtained including markings at observation position Pa. Just as before, the position coordinates of the two markings are calculated by image recognition. By comparing the position coordinates of the markings before and after the addition of the matrix, the amount of translational movement and rotation angle of the position where the specimen 4 is mounted on the specimen stage 2 are calculated. These data are stored in memory of the analysis control unit 27 as positional shift information.

When a person performing the analysis performs a predetermined operation on the operation unit 30, the control/processing unit 20 causes optical microscopy images of the specimen 4 prior to the addition of the matrix to be displayed on a screen of the display unit 31. Using operation unit 30, the person performing the analysis then specifies a two-dimensional area on the display screen where mass spectrometry imaging is to be performed. This determines the measurement range where mass spectrometry is to be performed. Then, under the control of the analysis control unit 27, mass spectrometry is sequentially performed on all measurement points that are included in the measurement range specified as described above. To explain, the analysis control unit 27 refers to the afore-described position shift information to correct the stage driving position, and uses the stage drive unit 9 and drive mechanism 6 to move the specimen stage 2 within the analysis position Pb. When a measurement point on specimen 4 moves to a laser irradiation position, a laser beam is irradiated for a short amount of time as afore-described, and various ions are released from the specimen 4. These ions are led to the vacuum chamber 14 and are sent to ion trap 17 via ion transport optical systems 15 and 16. The ions are temporarily held by the ion trap 17 and are then sent to the time-of-flight mass spectrometer 18. The ions arrive at detector 19 after being separated time-wise by the time-of-flight mass spectrometer 18 depending on the mass/charge ratio. The detector 19 outputs a detection signal that depends on the amount of ions that are incident to it. The detection signal is then input to the spectrum-processing unit 21.

The spectrum-processing unit 21 digitizes the detection signal and performs a predetermined data processing on the detection signal. Specifically, the spectrum-processing unit 21 creates a time-of-flight spectrum based on the detection signal for the particular measurement point, converts the time-of-flight to a mass/charge ratio and creates a mass spectrum. Furthermore, each spectrum is normalized based on the total ion count. The MS imaging data that is obtained in this manner is stored in the MS imaging data storage unit 223 of the data storage unit 22. A mass spectrum data is obtained as afore-described every time that the next measurement point inside the measurement range of the specimen 4 arrives at the laser irradiation position based on the movement of the specimen stage 2. The MS imaging data that is obtained is stored in the MS imaging data storage unit 223. In this way, MS imaging data is collected for all measurement points included within the measurement range.

After the mass spectrometry is performed, the person performing the analysis removes the specimen plate 3 from the specimen stage 2 and removes the matrix on the specimen 4. Also, with the specimen 4 still placed on the specimen plate 3, the person performing the analysis uses a predetermined staining reagent to stain the specimen 4, which has been removed of the matrix. After staining, the specimen plate 3 is returned to the specimen stage 2. Then, just as was done after the afore-described addition of the matrix, optical microscopy images (stained microscopy images) including markings are obtained at the observation position Pa with the image-capturing unit 7. The position coordinates of the two markings are then calculated by image recognition. By comparing the position coordinates of the two markings before and after the staining, the amount of translational movement and rotation angle of the mounting position of the specimen 4 on the specimen stage 2 are calculated. This is associated with the stained microscopy image data as the position shift information of the MS imaging image and the stained microscopy image and is stored in the stained image data storage unit 222.

Figure 2:
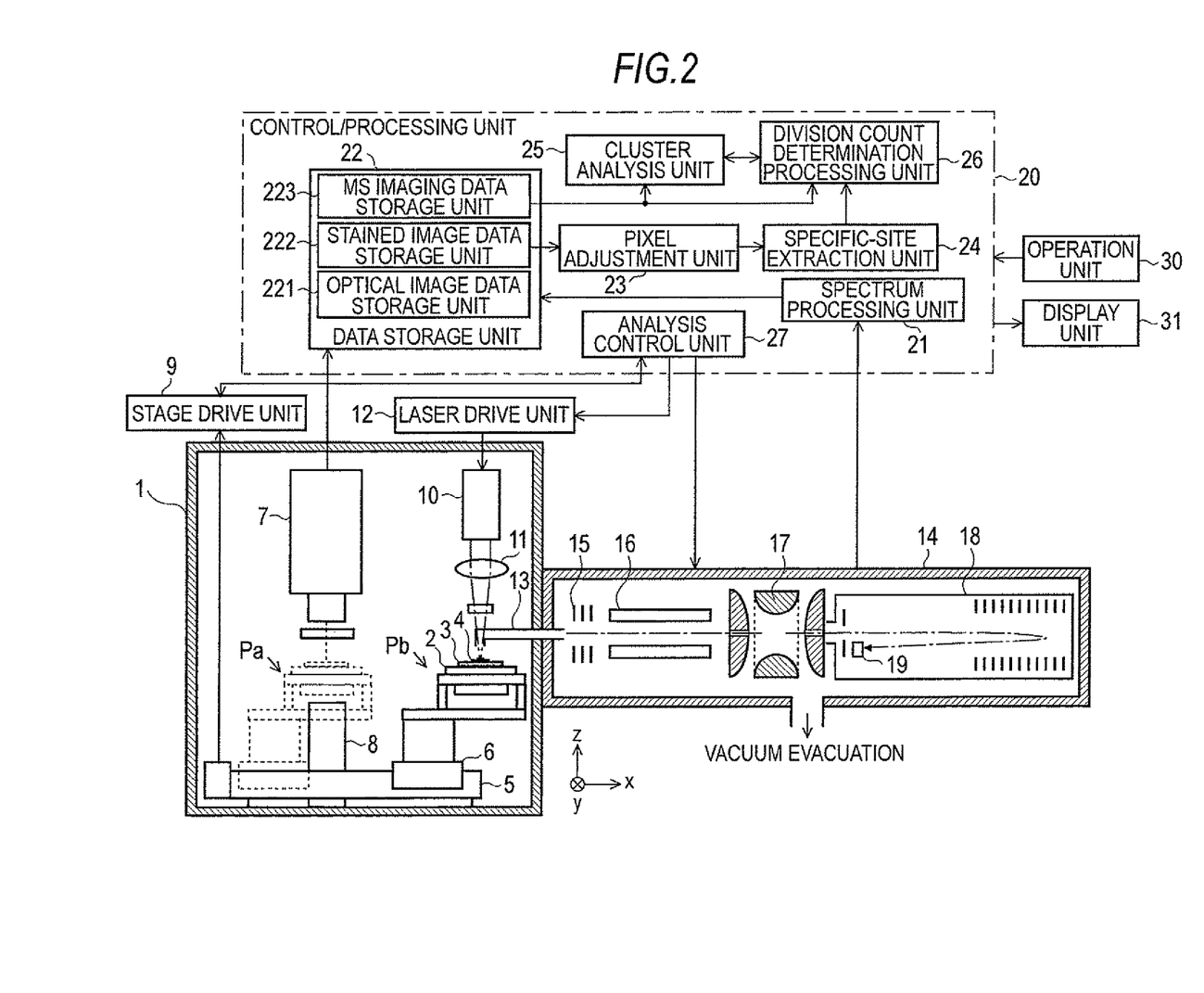
FIG. 2 shows a schematic view of the major components of another embodiment of an imaging mass spectrometer according to the present invention.

In another embodiment, as shown in FIG. 2, a microscope or a laser focusing optical system is set within the specimen chamber 1 at atmospheric pressure. The rest of the components are same or similar to those described in FIG. 1. With this configuration, the objective lens of the microscope can be made adjacent to the specimen surface, and the focal point can be shortened as well as the resolution of the microscopic image can be made higher. The laser beam can be irradiated on the specimen without going through the outer wall of the chamber. By this configuration, a resolution of 1 μm and a focal diameter of 5 μm were achieved.

Figure 3:
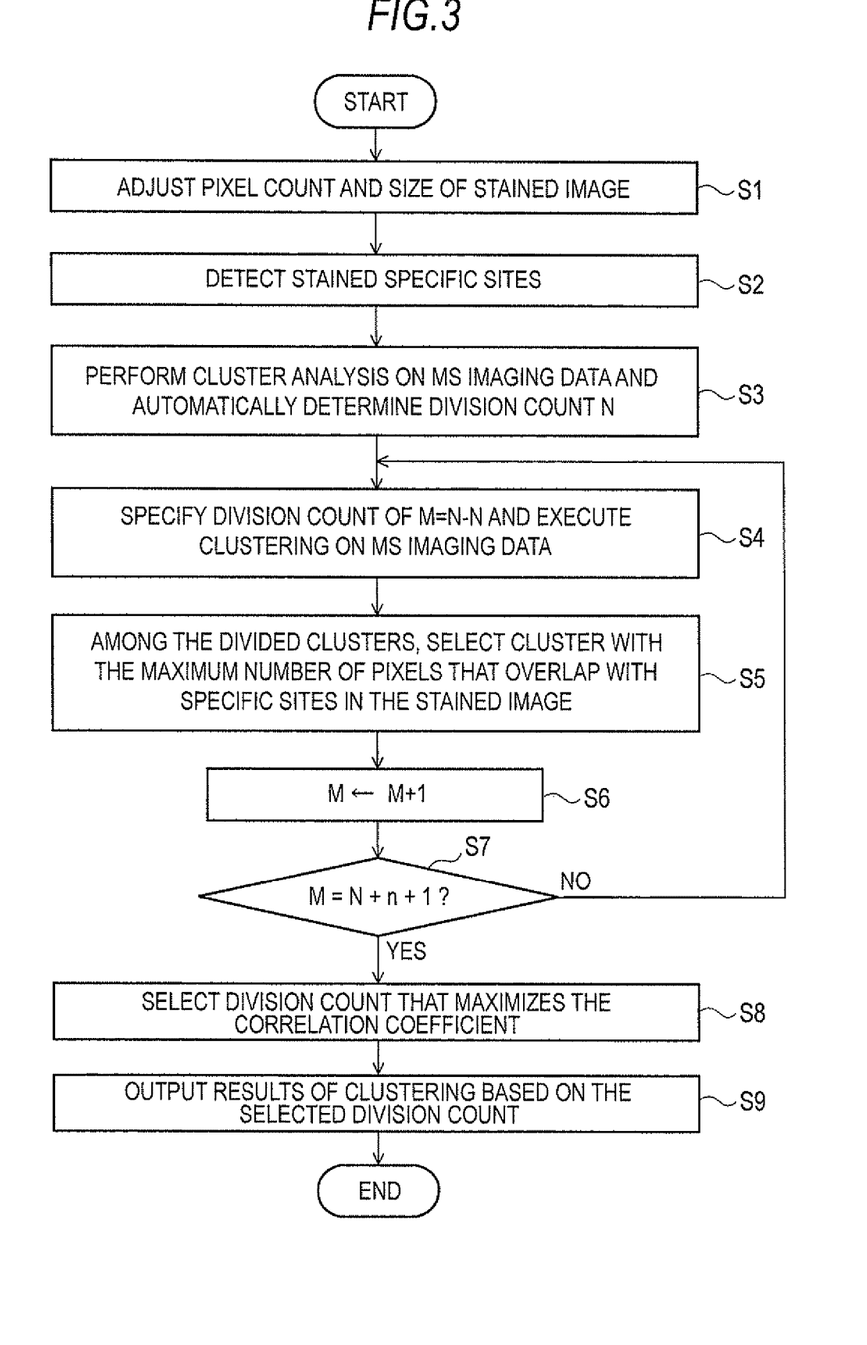
FIG. 3 is a flowchart showing a characteristic data processing in the present embodiment of an imaging mass spectrometer.
Figure 4:
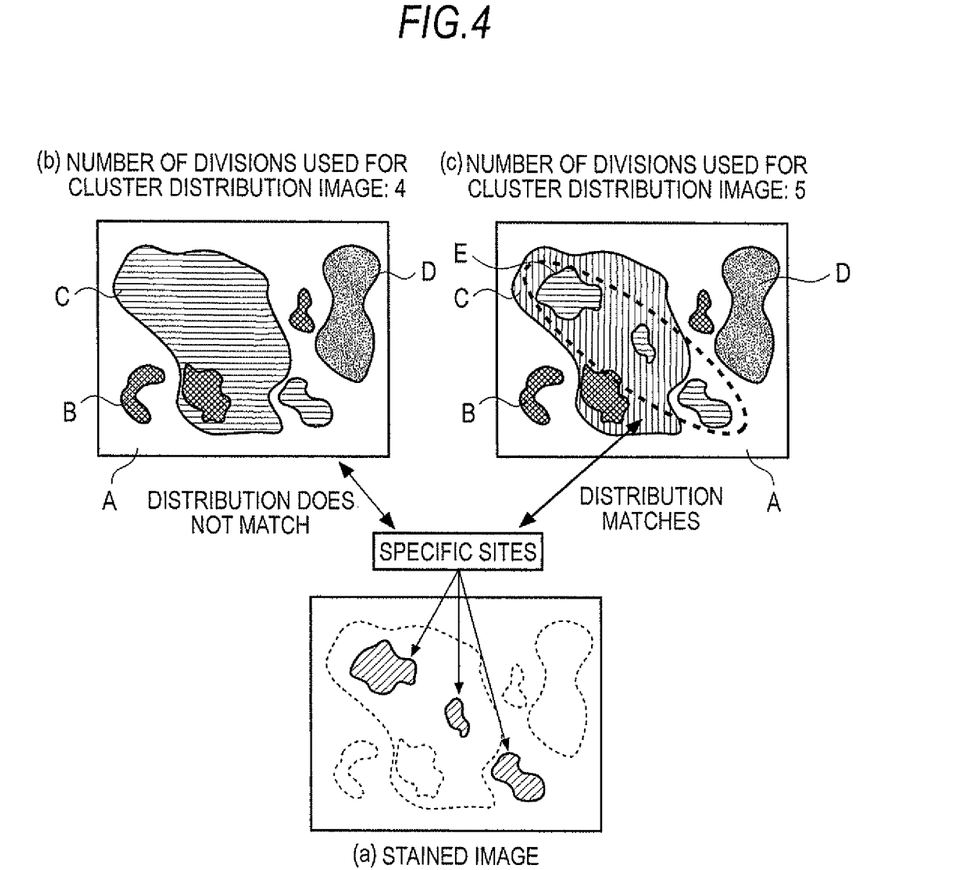
FIG. 4 shows the principle used in the division count determination in the present embodiment of an imaging mass spectrometer.

Next, with the MS imaging data and the stained microscopy image data for the same specimen 4 stored in the data storage unit 22 as afore-described, data processing is performed on the MS imaging data as shown in FIG. 3 through FIG. 6. FIG. 3 shows a flowchart of the characteristic data processing that is performed with the present embodiment of the imaging mass spectrometer. FIG. 4 shows the principle used behind the division count determination. FIG. 5 shows a conceptual view of the pixel adjustment process. FIG. 6 shows a conceptual view of the division count determination process.

First, FIG. 4 is used to explain the principle behind division count determination wherein a region on a MS imaging image is categorized into a plurality of micro-regions based on the use of a statistical process based on cluster analysis of the MS imaging data that is obtained from each micro-region.

Assume that FIG. 4(*a*) shows the stained microscopy image for a measurement region of specimen 4 where imaging mass spectrometry has been performed. The specific sites that were stained appear clearly in the stained microscopy image. Assume that FIG. 4(*b*) shows how the measurement region is divided when cluster analysis using a division count of 4 is performed on the mass spectrum data that is obtained from each of the micro-regions in the same measurement area. Also assume that FIG. 4(*c*) shows how the measurement region is divided when cluster analysis using a division count of 5 is performed on the same data. The mass spectrum data of the micro-regions that belong to the same clusters of A through E have been judged as being high in similarity under the afore-described division count conditions. During cluster analysis, the mass/charge ratio m/Z and signal strength for each peak are collected from the mass spectrum data, and a peak list is created. A cluster analysis is performed against the information in the peak list.

The stained specific sites shown in FIG. 4(*a*) include the same characteristic substance. Therefore, the MS imaging data of each pixel that corresponds to the specific site commonly includes the aforesaid characteristic substance, and if clustering is appropriately performed, each pixel should be categorized in a cluster that is independent and different from the other sites. Hence, the spatial distribution of the specific sites in the stained image and the similarity in the spatial distribution of the pixels in each of the clusters in the cluster distribution image were investigated. If the spatial distribution of all pixels that belong to any one cluster is similar to the spatial distribution of the specific sites in a stained image, the clustering is appropriate. That is, it can be judged that the division count that was used has a high reliability. In the example shown in FIG. 4, when the division count is 4 as shown in (*b*), there is no spatial distribution of all pixels that belong to any one cluster that matches the spatial distribution of the specific sites in the stained image. In contrast to this, when the division count is 5 as shown in (*c*), there is a good match between the spatial distribution of the specific sites in the stained image and the spatial distribution of all pixels that belong to cluster E. Hence, it can be judged that a division count of 5 is appropriate.

Figure 5A:
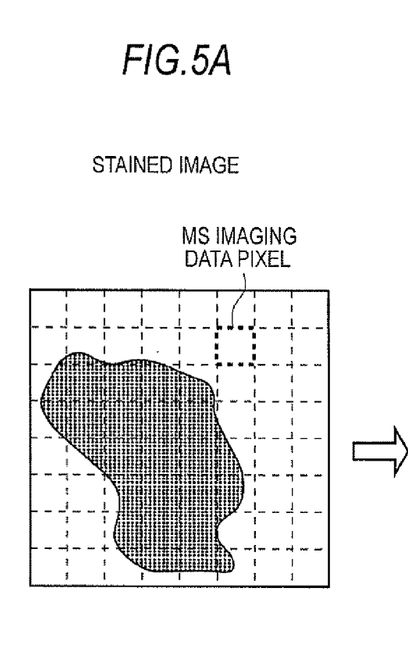
FIG. 5A shows a stained image partitioned according to the pixel size used in the imaging mass spectrometry.
Figure 5B:
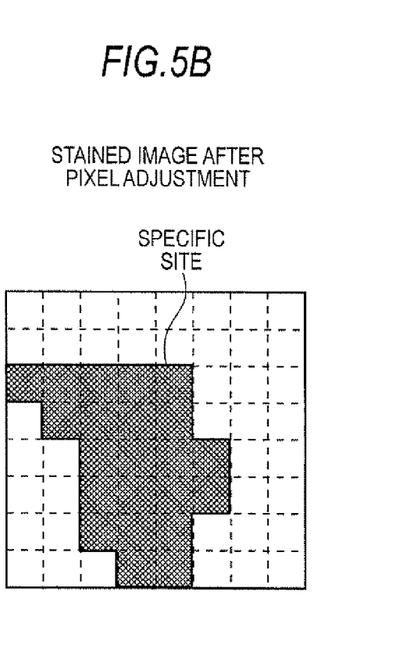
FIG. 5B shows a stained image after pixel adjustment.

The detailed procedure is described next with reference to FIG. 3. When data processing is instructed, the pixel adjustment unit 23 reads the stained microscopy image data from the stained image data storage unit 222, and performs adjustments so that the MS imaging data and the stained microscopy image data match each other in terms of the number of pixels and the pixel size (step S1). This is done because correlation is determined on a pixel by pixel basis between cluster distribution based on MS imaging data such as shown in FIGS. 4(*b*) and (*c*) and the spatial distribution of specific sites on a stained image such as shown in FIG. 4(*a*). In general, the pixel size in a MS imaging data is significantly larger than the pixel size of stained microscopy image. Therefore, for example, as shown in FIG. 5(*a*), the stained image is partitioned according to the pixel size used in the imaging mass spectrometry, and an average value is determined for the RGB values of the original pixels in the stained image that is included in each pixel. If the average value of the pixel falls within a specific range, the pixel is treated as a pixel from the stained specific site. In this way, it is possible to determine the stained image for each pixel shown in FIG. 5(*b*) from the stained image shown in FIG. 5(*a*).

Next, from the stained image that has been adjusted on a per pixel basis as afore-described, the specific-site extraction unit 24 extracts stained sites. That is, the specific-site extraction unit 24 extracts specific sites and acquires positional information of the pixels that are included in the specific sites (step S2).

Next, the cluster analysis unit 25 reads the MS imaging data from the MS imaging data storage unit 223, performs a cluster analysis on this data, categorizes each pixel into a plurality of clusters based on the degree of similarity of the mass spectrum data, and automatically determines the number of clusters N to divide into (step S3). For example, indices that can be used in determining the optimum division count in a cluster analysis include statistics such as pseudo F statistic and Beale's F statistic. These statistics can be simplified and be stated as representing the ratio between the variability between the average value of a cluster across different clusters and the variability between each element within a cluster. With an optimum division count, these statistics reach a local maximum. Hence, while performing clustering with a cluster analysis, each of the pixels is divided into a plurality of groups whose mass spectrum is similar, and the similarity of the mass spectrum is compared between groups, and similar groups are treated as a new group. This process is repeated to sequentially reduce the number of groups.

In that process, whenever the number of groups changes, the aforesaid statistics are determined in a search for a division count that causes the statistics to reach a local maximum. As for the method for the automatic determination of the division count, the k-means method that is disclosed in the afore-said Non-Patent Literature 2 can be used. However, the method used is not a limitation.

The division count N that is automatically decided in step S3 can serve as a guideline but is not necessarily an optimum value that can be used for categorizing the pixels. Therefore, the division count determination processing unit 26 cooperates with the cluster analysis unit 25 and uses steps S4 through S7 to search for an appropriate division count within the division count range of N±n. To explain, variable M representing the division count is first set to N−n, and cluster analysis is performed on the MS imaging data (step S4). After each of the pixels has been categorized, the cluster among M pieces of clusters that has the greatest number of pixels that overlap with a stained specific site within the stained images is selected, and a correlation coefficient is determined between the spatial distribution of the set that includes all pixels that are categorized into that cluster and the spatial distribution of the specific site (step S5). If the value of n is too large, the search range becomes too broad, and the calculation time becomes lengthy. On the other hand, if the value of n is too small, there is a risk that an optimum division count will not be found. Therefore, it is desirable to experimentally determine a suitable value of n, taking into account such factors as the type of target specimen.

FIG. 6 shows an example of how the correlation coefficient is determined. An image such as that shown in FIG. 6(a) showing the spatial distribution of a specific site is compared against an image representing the spatial distribution of pixels (identified with diagonal lines in FIG. 6(b) through (d)) belonging to the cluster corresponding to the image shown in FIG. 6(a). An evaluation score of "−1" is assigned to each pixel that exists only in one or the other of the images, and an evaluation score of "1" is assigned to each pixel that exists in both images. In other words, an evaluation score of "1" is assigned to each overlapping pixel, and the sum of the evaluation score is calculated for all pixels. For example, assume that FIG. 6(b) shows the image of the cluster corresponding to a specific site when using a division count of 2. In this case, since the number of pixels that exist only in one or the other of the images is 13 while 17 pixels are present in both images, the sum of the evaluation scores becomes 4. This is adopted as correlation coefficient An for a division count of 2.

Figure 6A:
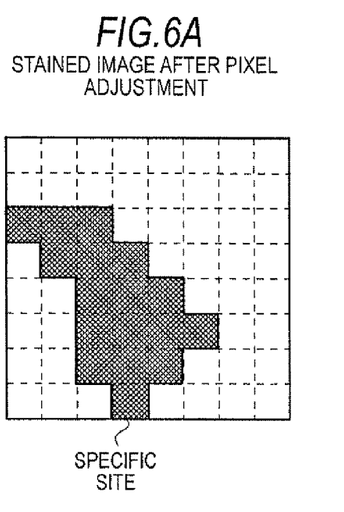
Figure 6B:
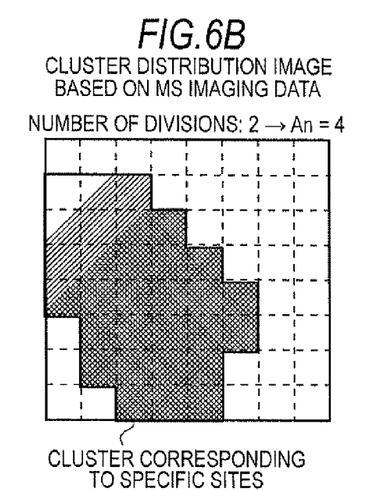
FIG. 6B shows a cluster distribution image based on the MS imaging data.
Figure 6C:
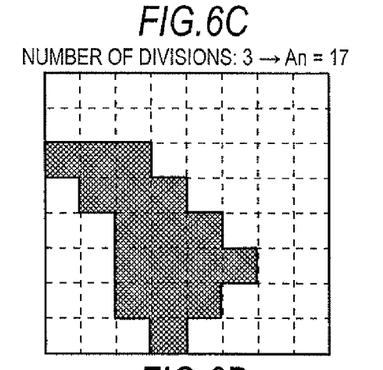
FIG. 6C shows a cluster distribution image with a different number of divisions.
Figure 6D:
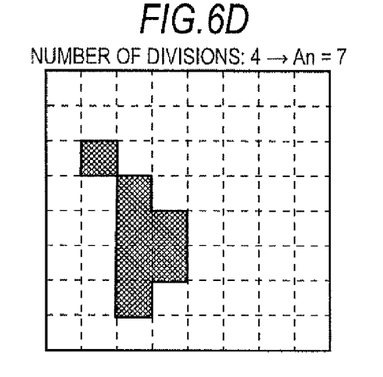
FIG. 6D shows a cluster distribution image with yet a different number of divisions.

Next, the variable M is incremented, and a decision is made as to whether or not variable M equals N+n+1 (steps S6 and S7). Step S7 is followed by step S4 until variable M becomes equal to N+n+1 so that the processes of the afore-described steps S4 and S5 are repeated. This means that the correlation coefficient An is calculated for the spatial distribution of the specific site and the spatial distribution of the pixels that are categorized in the cluster having the greatest number of pixels that overlap with the specific site in M pieces of clusters in an ascending order for variable M falling within the range from N−n to N+n. In the example shown in FIG. 6, if the division count is 3 or 4, the image of the cluster that correspond to the specific site is shown in (c) and (d), respectively. In this case, when the division count is 3, the correlation coefficient An is 17 while the coefficient An that is calculated is 7 for a division count of 4. Therefore, with this example, for a division count range of 2 to 4, the highest correlation coefficient An is obtained with N equal to 3 and n equal to 1 when the division count is 3.

If the decision in step S7 is "Yes," the division count determination processing unit 26 assumes that the division count that provides the highest correlation coefficient An is the optimum division count and selects that division count (step S8). In other words, the cluster division count is decided so that spatial distribution of the specific site that is extracted from the stained microscopy image and the spatial distribution of the pixels that belong to one cluster out of the plurality of clusters that are categorized into by the cluster analysis most resemble each other. Then, the result of the clustering based on the division count that is selected is displayed on display unit 31 using, for example, a color display image where different display colors are used for each cluster (step S9).

In the foregoing way, with the present embodiment of the imaging mass spectrometer, microscopy images that are obtained by staining or fluorescence labeling the specific sites that include much of a specific substance or includes a characteristic substance are referenced to derive cluster analysis results of a high reliability.

In the afore-described embodiment, even though a division count was selected that provided the largest correlation coefficient, if the correlation coefficients for different division counts are relatively close, the division count that provides the maximum correlation coefficient may not necessarily be the optimum. Because of this, it is also acceptable to select a plurality of division counts that provide a high correlation coefficient in step S8 and to simultaneously output the results that are clustered using the plurality of division counts in step S9. For example, it is acceptable to simultaneously display the results of cluster analysis using division counts of 4 through 6. In this way, even if the optimum division count cannot be narrowed down to one, the person performing the analysis only needs to check a limited number of results of the cluster analysis, thus greatly reducing the time and effort required in the analysis as compared to before.

Figure 7:
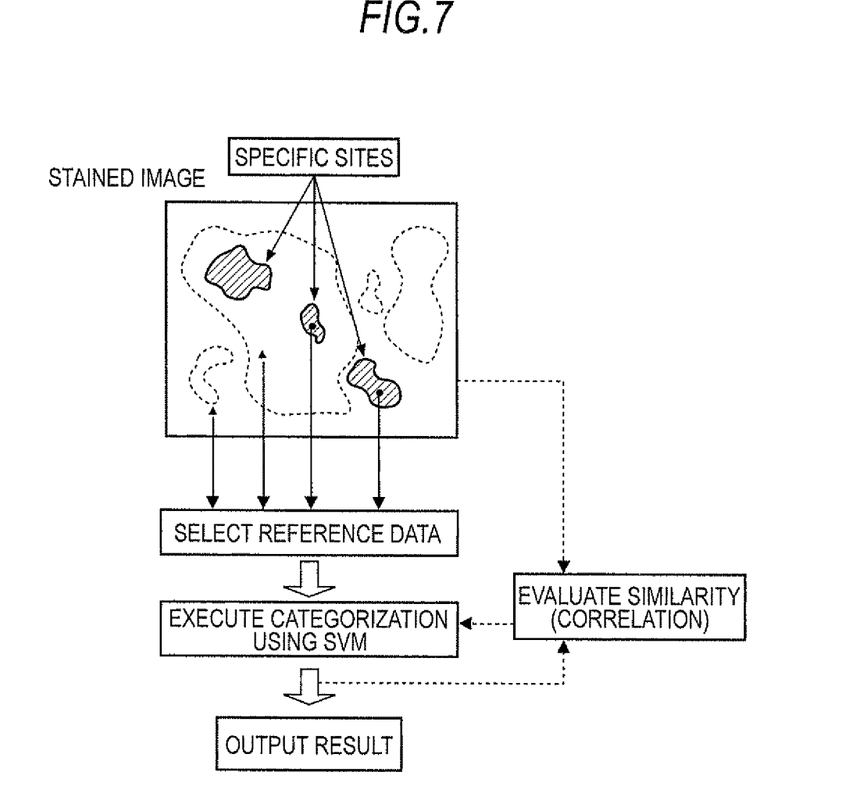
FIG. 7 shows a conceptual view of characteristic data processing used in another embodiment of an imaging mass spectrometer according to the present invention.

Next, another embodiment of the present invention wherein data processing of MS imaging data is performed using support vector machine instead of cluster analysis on an imaging mass spectrometer is described next with reference to FIG. 7. The points in a measurement area on specimen 4 where MS imaging data and stained microscopy image data are collected are the same as in the afore-described embodiment.

With a support vector machine, training data that can be used as a reference is required for categorizing the pixels based on MS imaging data. For that reason, after extracting stained specific sites in the stained images, mass spectrum data of the pixels that are included in the specific sites and mass spectrum data of pixels that are not in the specific sites are selected and used as training data, which is provided to the processing unit that executes the support vector machine. As shown in FIG. 7, a plurality of pixels that are included in the specific sites is selected, and data that is obtained by average or accumulating the mass spectrum data of the plurality of pixels may be used as the training data.

Using the afore-described training data, the support vector machine categorizes the individual pixels based on their mass spectrum data. The results may be output as is, but it is also possible to determine the similarity between the results (i.e., distribution image showing the pixel categorization) and the spatial distribution of specific sites within the stained image. If the similarity is judged to be low, this may be notified, or different training data may be automatically selected to repeat the process by the support vector machine. In this way, if a support vector machine is used, microscopy images that are obtained by staining or fluorescently labeling specific sites can be used both for the selection of training data and for the evaluation of the processed results.

The support vector machine is a typical learning algorithm that uses training data, but this is not a limitation, and other learning algorithms that use training data can similarly use stained images or fluorescent images to increase processing reliability or reduce the burden imposed on a person performing the analysis.

The afore-described embodiments are just examples of the present invention, and needless to say, modifications and additions can be made without deviating from the thrust of the invention and the scope of the claims of the present application.

DESCRIPTION OF THE NUMERICAL REFERENCES

1. Hermetically sealed chamber
2. Specimen stage
3. Specimen plate
4. Specimen
5. Guide
6. Drive mechanism
7. Image capturing unit
8. Transmitted-illumination unit
9. Stage drive unit
10. Laser beam irradiation unit
11. Laser focusing optical system
12. Laser drive unit
13. Ion transport tube
14. Vacuum chamber
15, 16. Ion transport optical system
17. Ion trap
18. Time-of-flight mass spectrometer
19. Detector
20. Control/processing unit
21. Spectrum processing unit
22. Data storage unit
221. Optical image data storage unit
222. Stained image data storage unit
223. MS imaging data storage unit
23. Pixel adjustment unit
24. Specific-site extraction unit
25. Cluster analysis unit
26. Division count determination processing unit
27. Analysis control unit
30. Operation unit
31. Display unit
Pa. Observation position
Pb. Analysis position

What is claimed is:

1. A mass spectrometry data processing method, said method comprising:
   generating mass spectrometry data that is obtained from each of a plurality of micro-regions that are set within a predetermined two-dimensional area on a specimen;
   extracting specific sites from microscopy images, which are obtained by labeling specific sites in said two-dimensional area or a portion thereof with a visualization marker;
   categorizing each of said micro-regions into a plurality of clusters based on similarity/dissimilarity of mass spectrometry data for each of the micro-regions so that micro-regions of high similarity belong to the same cluster; and
   determining the total number of clusters based on the results of a comparison between the spatial distribution of the specific sites that are extracted and the spatial distribution of all micro-regions that belong to one of the plurality of clusters into which each of said micro-regions are classified.

2. The mass spectrometry data processing method according to claim 1 wherein said determining the number of clusters evaluates the correlation between the spatial resolution of all micro-regions that belong to one of a plurality of clusters and the spatial distribution of the specific sites that are extracted and determines as the appropriate total cluster count either a sole total cluster count with the highest correlation or a predetermined number of total cluster counts that are selected after ranking in the order of high to low correlation.

3. The mass spectrometry data processing method according to claim 1 wherein: said categorizing each of said micro-regions determines an optimum total cluster count when categorizing each of the micro-regions into a plurality of clusters; and
   said determining the total number of clusters uses said optimum total cluster count as a guideline for a predetermined range of total cluster count and the spatial distribution of the specific sites to determine the appropriate total number of clusters.

4. The mass spectrometry data processing method according to claim 1 wherein the microscopy images that are obtained by labeling said specific sites with a visualization marker are stained microscopy images that are obtained by staining a specimen or fluorescent microscopy images that are obtained by observing with a fluorescence microscope after fluorescence labeling of the specimen.

5. A mass spectrometry data processing method, said method comprising:
   generating mass spectrometry data obtained from each of a plurality of micro-regions that are set within a predetermined two-dimensional area on a specimen;
   extracting specific sites from microscopy images, which are obtained by labeling specific sites in said two-dimensional area or a portion thereof with a visualization marker; and
   categorizing each of the micro-regions into a plurality of groups by using as reference data the mass spectrometry data that was obtained from micro-regions on the specimen that are included in a range of the specific sites that were extracted and by using a statistical learning method that is based on said reference data.

6. An imaging mass spectrometer for obtaining mass spectrometry data from each of a plurality of micro-regions that are set within a predetermined two-dimensional area on a specimen, said spectrometer comprising:
   a) an image-capturing means for acquiring microscopy images of a specimen wherein specific sites that are present within said two-dimensional area or a portion thereof have been marked with a visualization marker;
   b) a specific-site extraction means for extracting said specific sites from microscopy images that have been acquired by said image-capturing means;
   c) an analysis processing means for categorizing each of said micro-regions into a plurality of clusters based on similarity/dissimilarity of mass spectrometry data for each of the micro-regions so that micro-regions of high similarity belong to the same cluster; and
   d) a division count determination means for determining the total number of clusters used by said analysis processing means based on the results of a comparison between the spatial distribution of the specific sites that are extracted by said specific-site extraction means and the spatial distribution of all micro-regions that belong to one of the plurality of clusters into which each of said micro-regions are classified by said analysis processing means.

7. The imaging mass spectrometer according to claim 6 wherein said division count determination means evaluates the correlation between the spatial resolution of all micro-regions that belong to one of a plurality of clusters and the spatial distribution of the specific sites that are extracted by said specific-site extraction means and determines as the appropriate total cluster count either a sole total cluster count with the highest correlation or a predetermined number of total cluster counts that are selected after ranking in the order of high to low correlation.

8. The imaging mass spectrometer according to claim 6 wherein:
said analysis processing means determines the optimum total cluster count when categorizing each of the micro-regions into a plurality of clusters; and
said division count determination means uses said optimum total cluster count as a guideline for a predetermined range of total cluster count and the spatial distribution of the specific sites to determine the appropriate total number of clusters.

9. The imaging mass spectrometer according to claim 6 wherein the microscopy images that are obtained by said image-capturing means are stained microscopy images that are obtained by image capturing a stained specimen or fluorescence microscopy images that are obtained by fluorescence microscopy of the specimen that has been fluorescence labeled.

10. An imaging mass spectrometer for obtaining mass spectrometry data from each of a plurality of micro-regions that are set within a predetermined two-dimensional area on a specimen, said spectrometer comprising:
a) an image-capturing means for acquiring microscopy images of a specimen wherein specific sites that are present within said two-dimensional area or a portion thereof have been marked with a visualization marker;
b) a specific-site extraction means for extracting said specific sites from microscopy images that have been acquired by said image-capturing means; and
c) an analysis processing means for categorizing each of the micro-regions into a plurality of groups by using as reference data the mass spectrometry data that was obtained from micro-regions on the specimen that are included in a range of the specific sites that were extracted by said specific-site extraction means and by using a statistical learning method that is based on said reference data.

* * * * *